United States Patent [19]

Shah et al.

[11] Patent Number: 5,084,533
[45] Date of Patent: Jan. 28, 1992

[54] NEAT (SOLVENTLESS) HYDROGENATION OF 4-ACETOXYACETOPHENONE IN THE PRODUCTION OF 4-ACETOXYSTYRENE AND ITS POLYMERS AND HYDROLYSIS PRODUCTS

[75] Inventors: Bakulesh N. Shah, Corpus Christi, Tex.; Donna L. Keene, Carrollton, Va.

[73] Assignee: Hoechst Celanese Corporation, Somerville, N.J.

[21] Appl. No.: 558,023

[22] Filed: Jul. 25, 1990

Related U.S. Application Data

[62] Division of Ser. No. 221,145, Jul. 19, 1988, abandoned.

[51] Int. Cl.$^5$ .................................................. C08F 2/00
[52] U.S. Cl. ........................................ 526/75; 525/371
[58] Field of Search ........................... 526/75; 525/371

[56] References Cited

PUBLICATIONS

Corson et al., "Preparation of Vinylphenols and Isopropenylphenols", J. Org. Chem, 9–1957.

*Primary Examiner*—John C. Bleutge
*Assistant Examiner*—Mark Sweet
*Attorney, Agent, or Firm*—Shirley L. Church; Richard S. Roberts

[57] ABSTRACT

A process for the solventless (neat) hydrogenation of 4-acetoxyacetophenone to produce 4-acetoxyphenyl methylcarbinol. The reaction proceeds by heating at 54° C. to 120° C. with an excess of hydrogen in the presence of a Pd/C or activated nickel such as Raney Nickel catalyst in the absence of a solvent. The 4-acetoxyphenyl methylcarbinol may then be dehydrated to 4-acetoxystyrene. The later may be polymerized to poly(4-acetoxystyrene) and hydrolyzed to poly(4-hydroxystyrene).

5 Claims, No Drawings

NEAT (SOLVENTLESS) HYDROGENATION OF 4-ACETOXYACETOPHENONE IN THE PRODUCTION OF 4-ACETOXYSTYRENE AND ITS POLYMERS AND HYDROLYSIS PRODUCTS

This application is a divisional application of pending U.S. application Ser. No. 07/221,145, filed July 19, 1988, now abandoned.

BACKGROUND OF THE INVENTION

The present invention relates to a process for the neat hydrogenation of 4-acetoxyacetophenone in the production of 4-acetoxystyrene. The invention also pertains to a process for the polymerization, and hydrolysis thereof.

It is known in the art to produce monomers, homopolymers and copolymers of 4-acetoxystyrene and to hydrolyze the same to produce 4-hydroxystyrene derivatives or poly(4-hydroxystyrene). Such find use in the production of adhesives, coating compositions, photoresists and the like. The monomeric acetoxystyrene finds use as an intermediate in the production of such polymers as poly(4-acetoxystyrene) and poly(4-hydroxystyrene). These later compounds are useful as binder resins for photoresists. Alpha acetoxystyrene and beta acetoxystyrene are known per se and are described in U.S. Pat. No. 4,144,063 and acetoxymethylstyrene is taught in U.S. Pat. No. 3,963,495. U.S. Pat. No. 4,075,237 describes 1,4-dimethyl-2-hydroxystyrene, while U.S. Pat. No. 4,565,846 teaches the use of poly(3,5-dimethyl-4-hydroxystyrene).

Japanese patent 84023747 describes anti-static compounds employing poly-acetoxymethylstyrene and U.S. Pat. No. 4,221,700 describes a stabilized synthetic polymer composition using poly(alkylated alkenylphenol) including 2-methyl paravinyl phenol. U.S. Pat. Nos. 4,600,683 and 4,543,397 describe poly (alphamethyl vinylphenol). U.S. Pat. Nos. 4,517,028; 4,460,770 and 4,539,051 describe dimethyl vinyl phenol. The preparation of 4-hydroxystyrene is well known in the art. One process is described in U.S. Pat. No. 4,316,995 and another is described in U.S. Pat. No. 4,451,676.

Vinyl phenol may be prepared by a five step process of (1) acetylating phenol to p-hydroxyacetophenone, (2) acetylation of p-hydroxyacetophenone to p-acetoxyacetophenone, (3) hydrogenation to p-acetoxyphenyl methylcarbinol, (4) dehydration to p-acetoxystyrene, and (5) saponification to p-vinylphenol. The method is more fully described in Corson, B. B., et al, *Preparation of Vinylphenols and Isopropenylphenols*, J. Org. Chem., April 1958.

The prior art process for the hydrogenation of 4-acetoxyacetophenone to acetoxyphenyl methylcarbinol has been conducted with a Pd/C catalyst. However, this method has required the presence of such solvents as methanol and tetrahydrofuran. The required use of the solvent has been a problem in practice of this process Problems which have been experienced include the dissolution of the 4-acetoxyacetophenone in the solvent; increased reactor volume due to the presence of the solvent; subsequent removal of the Pd/C catalyst from the large volume of solvent in the 4-acetoxyphenyl methylcarbinol mixture; separation of the solvent from 4-acetoxyphenyl methylcarbinol; purification and recycling of the solvent; solvent losses; and by-products from the solvent. The present invention employs a process wherein the solvent is completely eliminated. It has been surprisingly found that the selectivity of the reaction is substantially not adversely affected by the elimination of the solvent component. Also, surprisingly other side reactions are not observed and an economical operation of the process is made possible.

SUMMARY OF THE INVENTION

The invention provides a method for producing 4-acetoxyphenyl methylcarbinol which comprises heating 4-acetoxyacetophenone at a temperature of from about 60° C. to about 90° C. in the presence of at least a stoichiometric amount of hydrogen, and a catalyst selected from the group consisting of Pd/C or activated nickel such as Raney Nickel in the absence of a solvent, for a sufficient time to produce 4-acetoxyphenyl methylcarbinol. The invention also provides a process for the production of 4-acetoxystyrene which comprises:

a) acylating phenol with acetic anhydride to produce 4-hydroxyacetophenone; and b) acylating the 4-hydroxyacetophenone with acetic anhydride to form 4-acetoxyacetophenone; and c) heating 4-acetoxyacetophenone at a temperature of from about 54° C. to about 120° C. in the presence of at least a stoichiometric amount of hydrogen, and a catalyst selected from the group consisting of Pd/C or activated nickel such as Raney Nickel in the absence of a solvent, for a sufficient time to produce 4-acetoxyphenyl methylcarbinol; and d) dehydrating the 4-acetoxyphenyl methylcarbinol to produce 4-acetoxystyrene.

The invention also provides a process for the production of poly(4-acetoxystyrene) which comprises subsequent free radical polymerization of the 4-acetoxystyrene to form poly(4-acetoxystyrene) having a molecular weight in the range of from about 1,000 to about 800,000, preferably about 5,000 to about 500,000.

The invention still further provides a process for the production of poly(4-hydroxystyrene) which comprises subsequently hydrolyzing the poly(4-acetoxystyrene) to form poly(4-hydroxystyrene) having a molecular weight in the range of from about 1,000 to about 500,000, preferably about 5,000 to about 500,000.

DETAILED DESCRIPTION OF THE PREFERRED EMBODIMENT

In the process for the production of 4-acetoxystyrene, one begins with phenol and acylates it with acetic anhydride and via a Friedel-Crafts catalysis or Fries rearrangement produces 4-hydroxyacetophenone. This 4-hydroxyacetophenone is then esterified with acetic anhydride to form 4-acetoxyacetophenone. The latter is then neat hydrogenated to form 4-acetoxyphenyl methylcarbinol. This is then dehydrated with an acid or base to form 4-acetoxystyrene monomer. Free radical polymerization and hydrolysis may follow.

A typical overall reaction sequence may be described schematically as follows:

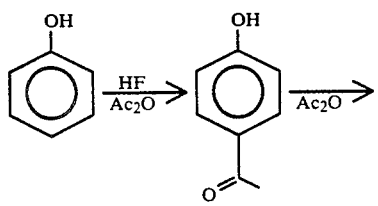

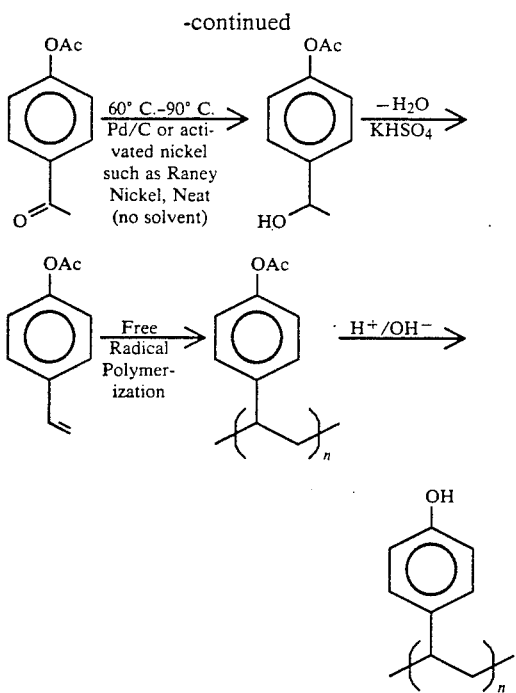

In the preferred embodiment the first reaction steps proceed as follows. One charges a reaction vessel with phenol and a slight excess of acetic anhydride and a Friedel-Crafts catalyst such as hydrogen fluoride. The acylation is conducted at a temperature of from about 5° C. to about 100° C., or more preferably from about 20° C. to about 80° C. A most preferred temperature is about 50° C. The reaction proceeds at a preferred pressure of from about 700 mm Hg to about 780 mm Hg for from about 1 to about 5 hours. Although hydrogen fluoride is the preferred catalyst, other Lewis acids may be also used such as $AlCl_3$, $BF_3$, $HClO_4$, $FeCl_3$ and $SnCl_4$. In the alternative, the acylation may be conducted by a Friss rearrangement, in a manner well known to the skilled artisan. The reaction product is 4-hydroxyacetophenone. This 4-hydroxyacetophenone is then esterified with acetic anhydride. In this process, the 4-hydroxyacetophenone is refluxed with an excess of acetic anhydride for from about 2 to about 20 hours. Excess acetic anhydride as well as generated acetic acid are removed by distillation in vacuo. This is conducted, for example at a pressure of from about 0.1 to about 1000 mm HgA and at an initial temperature of from about 135° C. to about 150° C., preferably from about 135° C. to about 145° C. which is then reduced to from about 35° C. to about 85° C.

The 4-acetoxyacetophenone is then neat hydrogenated to 4-acetoxyphenyl methylcarbinol. This is performed by heating 4-acetoxyacetophenone at a temperature of from about 54° C. to about 120° C. in the presence of at least a stoichiometric amount of hydrogen, and a catalyst selected from the group consisting of Pd/C or activated nickel such as Raney Nickel in the absence of a solvent, for a sufficient time to produce acetoxyphenyl methylcarbinol. In the more preferred embodiment, the reaction is conducted at a temperature of from about 60° C. to about 90° C. In the preferred embodiment, the reaction is conducted until substantial completion of hydrogenation as indicated by a lack of $H_2$ uptake, normally about 2 to 7 hours. In the preferred embodiment, when Pd/C is used, the reaction proceeds at a pressure of from about 14.7 psig to about 5000 psig, more preferably at a pressure of from about 50 psig to about 500 psig and most preferably at a pressure of from about 100 psig to about 400 psig. When activated nickel is used, the reaction proceeds at a pressure of from about 14.7 to about 5000 psig, more preferably from about 300 to about 600 psig and most preferably from about 350 to about 450 psig. Activated nickel is preferred since it can be recycled and a process with a higher selectivity can be attained.

This product is then dehydrated. Dehydration is preferably conducted by vacuum heating in the presence of a polymerization inhibitor and a dehydrating agent. In one preferred embodiment, the 4-acetoxyphenyl methylcarbinol is mixed with a $KHSO_4$ dehydrating agent and t-butyl catechol as a polymerization inhibitor. Other useful dehydrating agents non-exclusively include bases, $CuSO_4$, $CuCl_2$ and $Al_2O_3$. Other polymerization inhibitors non-exclusively include hydroquinone, phenothiazine, tetrachloroquinone, tert-butyl catechol and di-t-butyl-p-cresol. The dehydrating agent is present in an amount of from about 0.25 to about 5.0 percent weight of the 4-acetoxyphenyl methylcarbinol. The polymerization inhibitor is preferably present in an amount of from about 1% to about 5% based on the weight of the methylcarbinol. The reaction vessel is heated to from about 160° C. to about 230° C., preferably 170° C. to about 190° C. at a pressure of from about 0.1 to about 760 mm HgA. The resultant product is 4-acetoxystyrene with water as by product. The 4-acetoxystyrene monomer may then be polymerized by a free radical initiation process to produce poly(4-acetoxystyrene) such that it has a molecular weight in the range of from about 1,000 to about 800,000, preferably 5,000 to 500,000 or more preferably about 5,000 to about 300,000. This intermediate is then hydrolyzed with a base o acid to form poly(4-hydroxystyrene) such that it also has the aforesaid molecular weight range. One preferred free radical initiator is azobisisobutyronitrile. Other azo type initiators are also suitable. Still others nonexclusively include peroxides such as benzoyl peroxide, and di-t-butyl peroxide. It is predicted that essentially any free radical initiation system will serve in the same fashion. One preferred hydrolyzing agent is tetramethyl ammonium hydroxide. Other hydrolyzing agents non-exclusively include aqueous $NH_3$, NaOH, KOH, HCl, and $H_2SO_4$.

The following non-limiting examples serve to illustrate the invention.

EXAMPLE 1

75 grams of 4-acetoxyacetophenone and 7.5 g of Pd/C catalyst (5% Pd carbon) are charged in a 300-ml stirred reactor. The reactor is pressure checked with nitrogen at 150 psig. The nitrogen is then purged twice with 100 psig hydrogen. The hydrogen pressure is maintained at 100 psig. The reactor is then heated to 660° C. to carry out the reaction. After three hours of reaction time, the reaction is stopped by venting off hydrogen. A sample of the reaction mass is analyzed by gas chromatography. The analysis shows 4-acetoxyphenyl methylcarbinol 77.4%, unreacted 4-acetoxyacetophenone 6.6%, 4-ethylphenol 1.5%, 4-ethylphenyl acetate 0.2% and the balance is as due to other components.

EXAMPLE 2

12 kg of 4-acetoxyacetophenone and 450 g of Pd/C catalyst (5% Pd on carbon) are charged in a 5-gal stirred reactor. The 4-acetoxyacetophenone is melted before charging in the reactor. After pressure testing with nitrogen, the reactor is charged with hydrogen at 100 psig and the reactor contents are heated to 60° C. After 8 hours, the heat is turned off to stop the reaction. The product analysis by gas chromatography gives 92.3% 4-acetoxyphenyl methylcarbinol, 1.8% 4-ethylphenyl acetate, 0.3% 4-acetoxyacetophenone, 1.6% ethylbenzene and the balance is due to other components.

EXAMPLE 3

12 kg of 4-acetoxyacetophenone and 450 g of Pd/C catalyst (5% Pd on carbon) are charged in a 5-gal stirred reactor. The reactor is then charged with hydrogen at 80 psig and the reactor contents are then heated to 60° C. After 8 hours of reaction time, the reaction is stopped. The product analysis by gas chromatography gives 94% 4-acetoxyphenyl methylcarbinol, 1.3% ethylphenol, 1.2% 4-ethylphenyl acetate, 2.5% 4-acetoxyacetophenone and the balance is due to other components.

EXAMPLE 4

102 g of 4-acetoxyacetophenone and 10 g of Raney nickel catalyst are charged in a 300-ml stirred reactor. The reactor is then charged with hydrogen at 500 psig and heated to 60° C. for 270 minutes. The reactor is then cooled down and the product analyzed by gas chromatography. The analysis gives 80.4% 4-acetoxyphenyl methylcarbinol.

EXAMPLE 5

99.8 g of 4-acetoxyacetophenone and 4 g of Pd/C catalyst (5% Pd on carbon) are charged in a 300-ml stirred reactor. The reactor is then charged with hydrogen at 100 psig. The contents are heated to 60° C. After 4.25 hours, the reactor is cooled down and the product is analyzed by gas chromatography. The analysis is 94% acetoxyphenyl methylcarbinol, 2% ethylbenzene, 0.7% 4-ethylphenyl acetate and the balance is due to other components.

EXAMPLE 6

10 kg of melted 4-acetoxyacetophenone and 1.1 kg of Raney nickel catalyst are charged in a 20-1 stirred reactor. The contents are heated to 60° C. at 400 psig of nitrogen. The reactor is then charged with hydrogen. After 4 hours, the reactor is cooled down and the liquid product is analyzed by gas chromatography. The analysis is 97% acetoxyphenyl methylcarbinol, 0.1% ethylbenzene, 0.2% ethylphenyl acetate, 1.3% 4-acetoxyacetophenone and the balance is due to other components.

What is claimed is:

1. A process for the production of 4-acetoxystyrene which comprises:
   a) acylating phenol with acetic anhydride to produce 4-hydroxyacetophenone; and
   b) acylating the 4-hydroxyacetophenone with acetic anhydride to form 4-acetoxyacetophenone; and
   c) heating 4-acetoxyacetophenone at a temperature of from about 54° C. to about 120° C. in the presence of at least a stoichiometric amount of hydrogen, and a catalyst selected from the group consisting of Pd/C or activated nickel in the absence of a solvent, for a sufficient time to produce 4-acetoxyphenyl methylcarbinol; and
   d) dehydrating the 4-acetoxyphenyl methylcarbinol to produce 4-acetoxystyrene.

2. The method of claim 1 wherein the catalyst is Pd/C.

3. The method of claim 1 wherein the catalyst is Raney Nickel.

4. The method of claim 1 wherein the reaction step (c) is conducted until substantial completion of hydrogenation.

5. The method of claim 1 wherein the reaction step (c) is conducted at a pressure of from about 14 psig to about 5,000 psig.

* * * * *

UNITED STATES PATENT AND TRADEMARK OFFICE
CERTIFICATE OF CORRECTION

PATENT NO. : 5,084,533
DATED : January 28, 1992
INVENTOR(S) : Bakulesh N. Shah, Donna L. Keene It is certified that error appears in the above-identified patent and that said Letters Patent is hereby corrected as shown below:

Column 3, line 41:   "Friss" should read --Fries--

Column 4, line 39:   "o" should read --or--

Column 4, line 61:   "to660°C" should read --to 60°C.--

Signed and Sealed this

Twentieth Day of April, 1993

Attest:

MICHAEL K. KIRK

Attesting Officer

Acting Commissioner of Patents and Trademarks